(12) United States Patent
Jeung (10) Patent No.: US 8,135,205 B2
(45) Date of Patent: Mar. 13, 2012

(54) RAPID MATCHING OF NOISY SPECTRA OR OTHER SIGNAL PATTERNS

(75) Inventor: Andrew G. Jeung, Mountain View, CA (US)

(73) Assignee: Varian Medical Systems, Inc., Palo Alto, CA (US)

( * ) Notice: Subject to any disclaimer, the term of this patent is extended or adjusted under 35 U.S.C. 154(b) by 578 days.

(21) Appl. No.: 12/340,685

(22) Filed: Dec. 20, 2008

(65) Prior Publication Data

US 2010/0158385 A1 Jun. 24, 2010

(51) Int. Cl.
*G06K 9/00* (2006.01)
(52) U.S. Cl. .................................................... 382/141
(58) Field of Classification Search .............. 382/141, 382/143
See application file for complete search history.

(56) References Cited

U.S. PATENT DOCUMENTS

| 6,266,390 | B1 * | 7/2001 | Sommer et al. | 378/45 |
| 6,519,315 | B2 * | 2/2003 | Sommer et al. | 378/45 |
| 6,888,917 | B2 * | 5/2005 | Sommer et al. | 378/58 |
| 7,606,667 | B2 * | 10/2009 | Herold et al. | 702/22 |
| 2008/0128607 | A1 * | 6/2008 | Herold et al. | 250/282 |

* cited by examiner

*Primary Examiner* — Roy M Punnoose
(74) *Attorney, Agent, or Firm* — Vista IP Law Group, LLP.

(57) ABSTRACT

A method for use in an object scanning process includes obtaining a reference spectrum that includes a plurality of reference peaks, and comparing the reference spectrum with an input spectrum that has a plurality of input peaks, wherein a number of the reference peaks is less than eight. A method for use in an object scanning process includes obtaining a reference spectrum that includes a plurality of reference peaks, comparing one of the reference peaks with a plurality of input peaks from an input spectrum, comparing another one of the reference peaks with the plurality of input peaks from the input spectrum, and determining a degree of similarity between the reference spectrum and the input spectrum using a result from the acts of comparing.

48 Claims, 6 Drawing Sheets

RAPID MATCHING OF NOISY SPECTRA OR OTHER SIGNAL PATTERNS

FIELD

This application relates generally to object scanning, and more specifically, to systems and methods for identifying substance from an object scan.

BACKGROUND

The events of Sep. 11, 2001 forced recognition of an urgent need for more effective and stringent screening of airport baggage. The need for security expanded from the inspection of carry-on bags for knives and guns to the complete inspection of checked bags for a range of hazards with particular emphasis upon concealed explosives. The demonstrated willingness of terrorists to die in the pursuit of their aims meant that 100% passenger-to-bag matching, which could be put in place rapidly, was not sufficient to counter an attempt to conceal explosives in checked baggage and bring down an airliner. Successful screening for the presence of explosives presents numerous technological challenges, many of which are not met in present systems. For example, existing systems do not, and cannot, scan luggage rapidly and accurately for detecting the presence of explosives and hazardous materials. This is because data from a luggage scan may have a low signal-to-noise ratio, making it difficult to accurately scan the luggage. Also, since a luggage scan may require a comparison of the luggage content against a large number of reference substances, which require significant time, existing luggage scan may not be able to be performed rapidly.

SUMMARY

In accordance with some embodiments, a method for use in an object scanning process includes obtaining a reference spectrum that includes a plurality of reference peaks, and comparing the reference spectrum with an input spectrum that has a plurality of input peaks, wherein a number of the reference peaks is less than eight.

In accordance with other embodiments, a system for use in an object scanning process includes a processor configured for obtaining a reference spectrum that includes a plurality of reference peaks, and comparing the reference spectrum with an input spectrum that has a plurality of input peaks, wherein a number of the reference peaks is less than eight.

In accordance with other embodiments, a method for use in an object scanning process includes obtaining a reference spectrum that includes a plurality of reference peaks, comparing one of the reference peaks with a plurality of input peaks from an input spectrum, comparing another one of the reference peaks with the plurality of input peaks from the input spectrum, and determining a degree of similarity between the reference spectrum and the input spectrum using a result from the acts of comparing.

In accordance with other embodiments, a system for use in an object scanning process includes a processor configured for obtaining a reference spectrum that includes a plurality of reference peaks, comparing one of the reference peaks with a plurality of input peaks from an input spectrum, comparing another one of the reference peaks with the plurality of input peaks from the input spectrum, and determining a degree of similarity between the reference spectrum and the input spectrum using a result from the acts of comparing.

In accordance with other embodiments, a method for use in an object scanning process includes obtaining a reference spectrum that includes a reference peak, comparing the reference peak with an input peak from an input spectrum, wherein the act of comparing comprises determining information regarding a positional match between the reference peak and the input peak, and information regarding a magnitude match between the reference peak and the input peak, and using a result from the act of comparing to determine a degree of similarity between the reference spectrum and the input spectrum.

In accordance with other embodiments, a system for use in an object scanning process includes a processor configured for obtaining a reference spectrum that includes a reference peak, and comparing the reference peak with an input peak from an input spectrum, wherein the act of comparing comprises determining information regarding a positional match between the reference peak and the input peak, and information regarding a magnitude match between the reference peak and the input peak, and using a result from the act of comparing to determine a degree of similarity between the reference spectrum and the input spectrum.

Other and further aspects and features will be evident from reading the following detailed description of the embodiments, which are intended to illustrate, not limit, the invention.

BRIEF DESCRIPTION OF THE DRAWINGS

The drawings illustrate the design and utility of embodiments, in which similar elements are referred to by common reference numerals. These drawings are not necessarily drawn to scale. In order to better appreciate how the above-recited and other advantages and objects are obtained, a more particular description of the embodiments will be rendered, which are illustrated in the accompanying drawings. These drawings depict only typical embodiments and are not therefore to be considered limiting of its scope.

DESCRIPTION OF THE EMBODIMENTS

Various embodiments are described hereinafter with reference to the figures. It should be noted that the figures are not drawn to scale and that elements of similar structures or functions are represented by like reference numerals throughout the figures. It should also be noted that the figures are only intended to facilitate the description of the embodiments. They are not intended as an exhaustive description of the invention or as a limitation on the scope of the invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated.

The embodiments described herein provide a technique to compute a degree of similarity between a noisy spectrum and a reference spectrum. The noisy spectrum (input spectrum) may be an experimentally determined spectrum, or a spectrum generated for practical purposes, such as a spectrum from an object scanning, etc. The reference spectrum can be previously measured or it can come from a known or published library of spectra for matching. The computation is such that the measured spectrum can have extra peaks without influencing the computed degree of similarity. Therefore, it is ideal for cases in which the measured spectrum is from a mixture of compounds, and one is interested in determining whether the mixture contains a compound that is associated with the reference spectrum (e.g., a compound that is desired to be detected in the mixture).

Figure 1:
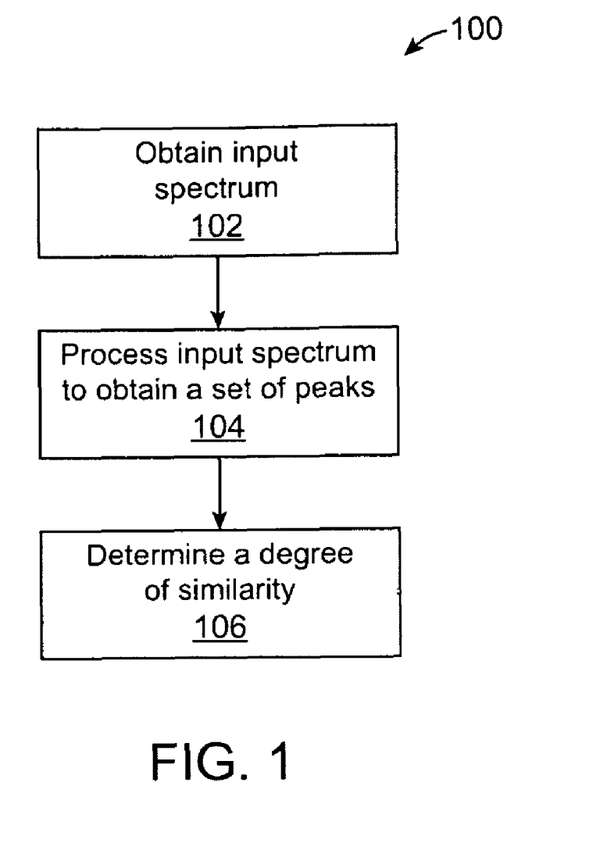
FIG. 1 illustrates a method for determining a degree of similarity between an input spectrum and a reference spectrum in accordance with some embodiments.
Figure 2:
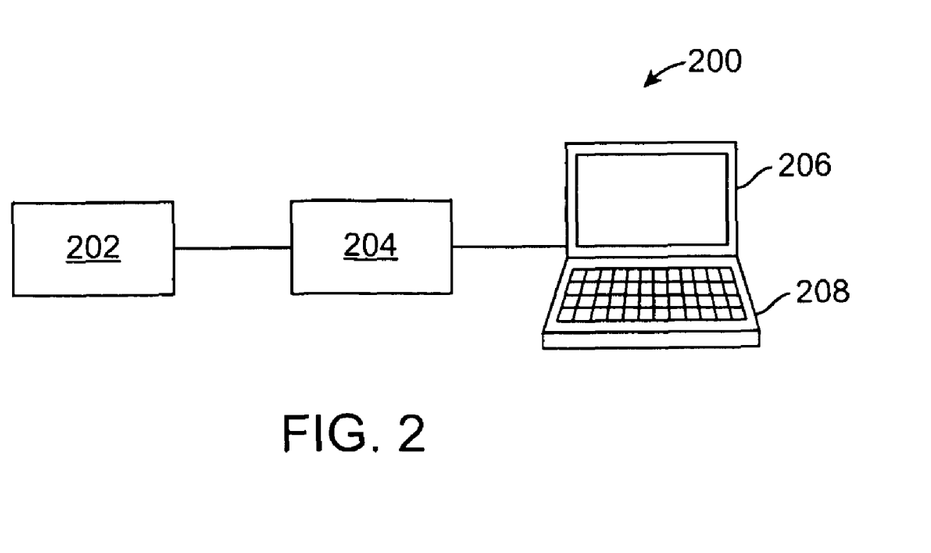
FIG. 2 illustrates a scanning system with a processor for performing embodiments of the functions described herein.

FIG. 1 illustrates a method 100 for determining a degree of similarity between an input spectrum and a reference spectrum in accordance with some embodiments. First, the input spectrum is obtained (step 102). In the illustrated embodiments, the input spectrum is obtained by a processor 204 receiving data regarding the input spectrum. The processor 204 may be a part of a scanning system 200, that includes a scanning machine 202, which generates the input spectrum (FIG. 2). In the illustrated embodiments, the scanning machine 202 is a luggage scanning machine. However, in other embodiments, the scanning machine 202 may be other types of scanning machine, such as a machine for scanning patients for medical purposes. Also, in other embodiments, the processor 204 need not be a part of the scanning system 200, and instead, it may be a part of a processing system that is separate from the scanning system 200. In such cases, the processor 204 is configured to receive information from the scanning system 200, e.g., using a cable or a wireless communication device. Further, in other embodiments, the input spectrum may have been already previously generated and stored in a medium. In such cases, the act of obtaining the input spectrum in step 102 may be accomplished by the processor 204 retrieving from the medium data for the input spectrum. Also, in further embodiments, the processor 204 may be integrated with the scanning machine 202. Devices for generating input spectrum are well known, and therefore, will not be described in detail. As shown in FIG. 2, the scanning system 200 may further include a user interface, which includes a screen 206 for displaying information (e.g., graphics that represent the input spectrum) to a user, and a keyboard 208 for allowing the user to input information (e.g., any of the information described herein).

Next, the input spectrum is processed to reduce or convert the input spectrum into a discrete set of peaks (step 104). In the illustrated embodiments, the processor 204 is configured (e.g., programmed and/or built) to smooth the original input spectrum using a Savitsky-Golay smoothing filter, perform a standard background subtraction, and then use the second derivative to determine (e.g., identify) peak locations. Each of the peaks are expressed as (x,y) pairs in which x represents the peak position and y represents the peak amplitude. In the case of X-ray diffractometry, the peak position may be measured in d-spacing units (Angstroms) for easy comparison with reference spectra, such as those available in literatures or computer databases.

In any embodiments described herein, the discrete set of peaks (input peaks) may themselves be considered as the input spectrum. Thus, as used in this specification, the term "input spectrum" may refer to the original measured spectrum, or a set of peaks that are obtained from processing of the original measured spectrum. In some embodiments, the input spectrum is obtained by scanning an object (which may be a solid, a liquid, a gel, or any other materials) that has a mixture of substances, and the input spectrum may have a plurality of sets of peaks, with each of the sets representing a substance in the mixture.

Next, the processor 204 determines a degree of similarity between peaks from the input spectrum and peaks from a reference spectrum (step 106). The reference spectrum represents a substance, such as an explosive, or a hazardous chemical, that is desired to be detected in the material being tested. The reference spectrum could be determined using the same or similar technique described above. For example, in some embodiments, a known compound sample may be scanned to generate a reference spectrum, and the reference spectrum may be processed to reduce it to a discrete set of reference peaks as described above. In any embodiments described herein, the discrete set of reference peaks may themselves be considered as the reference spectrum. Thus, as used in this specification, the term "reference spectrum" may refer to the original reference spectrum, or a set of reference peaks that are obtained from processing of the original reference spectrum. In other embodiments, a library, such as a database, of reduced spectra for known compounds that are desired to be matched may be used to provide the reference spectrum. In the case of X-ray diffractometry, libraries such as the Powder Diffraction File (PDF) from the International Center for Diffraction Data (ICDD) are readily available for use.

In the illustrated embodiments, the processor 204 is configured (e.g., programmed and/or built) to compute a prenormalized match score using the equation:

$$\text{score} = \sum_i \left[ y_{r,i} \cdot \sum_j \left( e^{-\left(\frac{x_{r,i} - x_{m,j}}{a}\right)^2} e^{-\left(\frac{\ln(y_{r,i}/y_{m,j})}{b}\right)^2} \right) \right]$$

where $(x_{r,i}, y_{r,i})$ is the position and magnitude of the i'th peak in the reference spectrum and $(x_{m,j}, y_{m,j})$ is the position and magnitude of the j'th peak in the input spectrum. The values of a and b may be any constants set to suit a particular application. In some embodiments in which X-ray diffractometry is used, the value 0.005 Å is used for the variable a, and 1.5 is used for the variable b. In some embodiments, the processor 204 may provide a user interface (e.g., graphics in screen 206) that allows the user to input information for use in the equation, or to adjust the equation.

The above scoring technique provides several advantageous features. The first exponential term is for measuring a degree of match of the positional values between peaks from the reference spectrum and peaks from the input spectrum. The second exponential term is for measuring a degree of match of the intensity/magnitude between peaks from the reference spectrum and peaks from the input spectrum. Thus, both the positional values and the intensity values of the peaks are considered. Based on the above scoring algorithm, the score drops exponentially as a peak (input peak) from the input spectrum is more distant from a peak (reference peak) from the reference spectrum. Also, the match score drops exponentially with the ratio of the peak heights. Thus, the peaks from the input spectrum and the reference spectrum will have a small match score if they are either far away from each other in position (meaning that their energy or d-spacing is very different) or far away from each other in intensity (meaning they are not the same height).

Figure 3A:
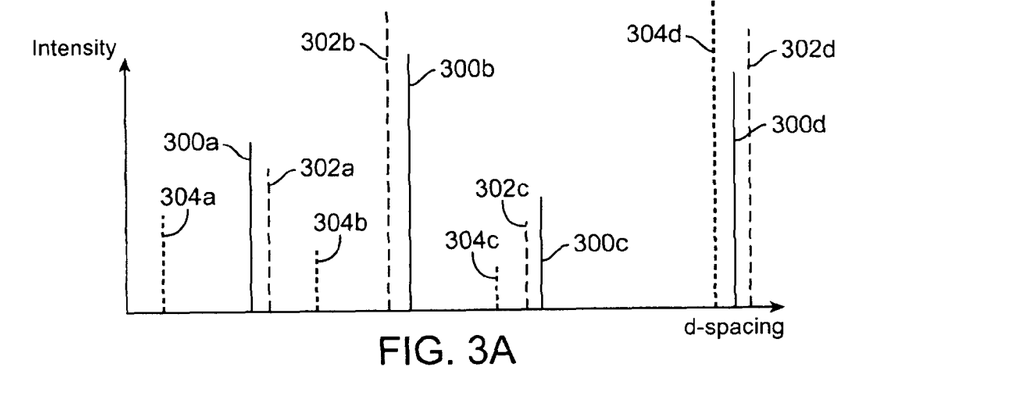
FIGS. 3A-3C illustrates the concept of the technique used in the method of FIG. 1.
Figure 3B:
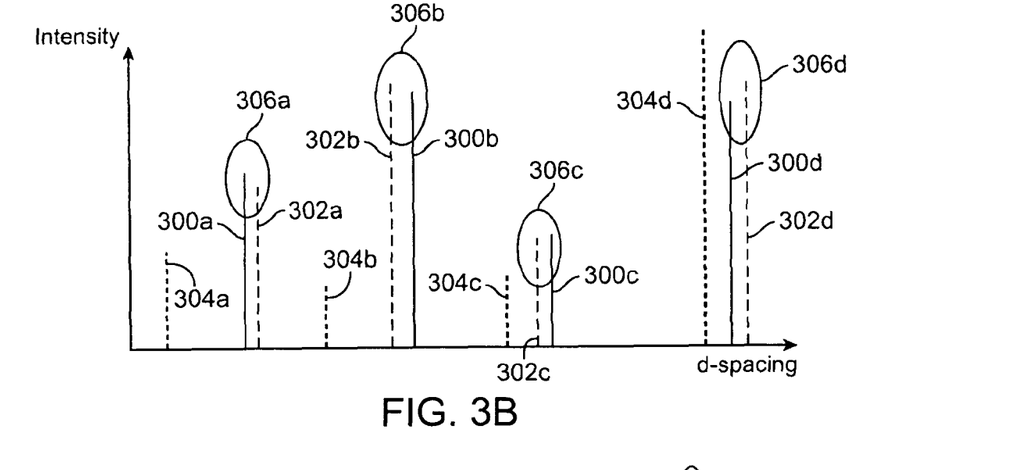
Figure 3C:
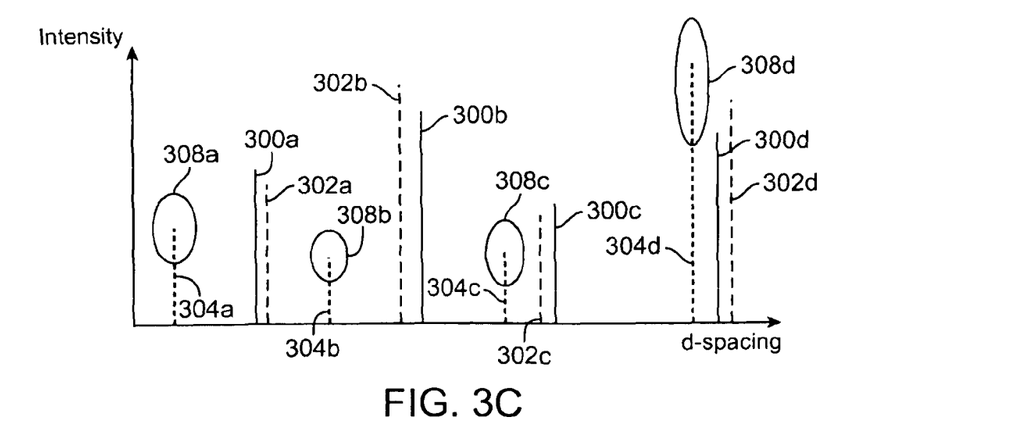

FIGS. 3A-3C illustrate the above concept. FIG. 3A illustrates an input spectrum 300 that is superimposed with a first reference spectrum 302 and a second reference spectrum 304 for comparison. In some embodiments, the screen 206 may display such graphics to a user for allowing visualization of the comparison between the input spectrum and various reference spectra. The input spectrum 300 includes five input peaks 300a-300d. In the illustrated example, each peak 300 is illustrated as a line. However, it should be noted that in other examples, each peak may have other configurations, such as a curve with a crest. Also, in other embodiments, the peak needs not have any configuration, and may be represented by a value or a point. Thus, as used in this specification, the term "peak" may refer to a line, a curve, a point, a value, anything that has a crest characteristic, anything that can be used to represent a crest characteristic, or anything that may be reduced to a point (such as a point with a position and a value) or a line (such as a line with a position and a height). The first reference spectrum 302 represents a first substance that is desired to be detected, and includes five reference peaks 302a-302d. The second reference spectrum 304 represents a second substance that is desired to be detected, and includes five reference peaks 304a-304d.

FIG. 3B illustrates a comparison between the input spectrum 300 and the first reference spectrum 302. A comparison field 306 is created at the end of each reference peak 302 to illustrate the spectrum comparison graphically. The width of the comparison field 306 represents a positional match threshold, wherein if an input peak is within the width of the comparison field, then the positional match may be considered good, and if an input peak is outside the width, then the positional match may be considered poor. The length of the comparison field 306 correlates with a length (or magnitude/intensity) of the reference peak 302, in which the higher the reference peak 302, the longer the comparison field 306 is provided. This places more emphasis on matches for higher reference peaks. This is because matches for the lower reference peaks may not be a strong indication that the material being tested includes the reference substance. As illustrated in the example, the tips of the input peaks 300a-300d are within the respective comparison fields 306 of the reference peaks 302a-302d. This indicates that there is a good match between the input spectrum 300 and the first reference spectrum 302. If the above described scoring technique is used, the resulting score would provide a relatively high value, indicating a high degree of match between the input spectrum 300 and the reference spectrum 302.

FIG. 3C illustrates a comparison between the input spectrum 300 and the second reference spectrum 304. Comparison field 306 is created at the end of each reference peak 304 to illustrate the spectrum comparison graphically. As illustrated in the example, the tips of the input peaks 300a-300d are outside the respective comparison fields 306 of the reference peaks 304a-304d. This indicates that there is a poor match between the input spectrum 300 and the second reference spectrum 304. If the above described scoring technique is used, the resulting score would provide a relatively low value, indicating a low degree of match between the input spectrum 300 and the reference spectrum 304. Thus, in the above examples, it may be concluded that the material for the input spectrum 300 contains the first substance desired to be detected (represented by the first spectrum 302), and does not contain the second substance desired to be detected (represented by the second spectrum 304).

Returning to the above equation, the factor of $y_r$ in the beginning of the above equation is a weighting factor. It is used to make the matching of a relatively intense (higher) peak in the reference spectrum count more than a matching of a relatively shorter peak. This is advantageous because matching of higher peaks correlates with a higher probability that the unknown object being scanned contains a substance (which is represented by the input spectrum) matches with a known substance desired to be detected (which is represented by the reference spectrum).

In the above scoring technique, each of the peaks from the reference spectrum is compared with a plurality of the peaks from the input spectrum. Such technique for measuring a degree of similarity is based on a "reverse" matching in which each peak in the reference spectrum is compared against a plurality of peaks in the input spectrum, not the other way around. Therefore, the overall match score is much lower if the input spectrum has missing peaks that are in the reference spectrum, but not necessarily lowered if the input spectrum has extra peaks that are not in the reference spectrum. This is particularly useful in the situation in which the input spectrum may represent a mixture of compounds, but only one or a subset of which is desired to be detected. For example, a mixture may include 50 input peaks, among which, 5 input peaks are from substance S1, 4 input peaks are from substance S2, and the remaining input peaks may be from other substances or noise. Using the reverse matching technique described, a reference spectrum (having 5 reference peaks) representing substance S1 is compared against the 50 input peaks. If one of the 5 peaks in the reference spectrum is missing in the input spectrum, the overall match score for substance S1 would be lower (compared to if all 5 peaks are found in the input spectrum). On the other hand, because of the reverse matching technique, the remaining 45 peaks from the input spectrum would not affect the match score. Similarly, a reference spectrum (having 4 reference peaks) representing substance S2 is compared against the 50 input peaks using the reverse matching technique. If one of the 4 peaks in the reference spectrum is missing in the input spectrum, the overall match score for substance S2 would be lower (compared to if all 4 peaks are found in the input spectrum). On the other hand, because of the reverse matching technique, the remaining 46 peaks from the input spectrum would not affect the match score.

In some embodiments, when performing step 106, the processor 204 may be configured to normalize the score. For example, the match of the reference spectrum to itself may be defined to be unity (or some other standard value). In such cases, the processor may be configured to divide the score determined using the above equation by another score that is determined by matching the reference spectrum against itself. This normalization makes comparison of match scores across compounds easier. This is because a match for a certain substance may always produce a relatively low score, while a match for another substance may always produce a relatively high score. As a result, without normalizing the score, the score itself may not be able to reflect a degree of match meaningfully. In some embodiments, the processor 204 may provide a user interface (e.g., graphics in screen 206) that allows the user to input information for prescribing how the score should be normalized.

In some cases, the reference spectrum is processed to obtain a set of peaks that includes only a prescribed number of the largest peaks in the reference spectrum. In such cases, the relatively smaller peaks are excluded from the reference spectrum. For example, if the prescribed number is 8, then the processor is configured to determine the eight largest peaks from the reference spectrum, and use them for comparison, while excluding the remaining smaller peaks from the set. Thus, as used in this specification, the term "reference spectrum" may refer to a reference spectrum in which the number of reference peaks have not been reduced, or to a processed reference spectrum in which the number of reference peaks have been reduced. In the illustrated embodiments, the reference spectrum is limited to having less than 8 peaks, and more preferably, less than 6 peaks, such as 4 or 5 peaks. This is advantageous in that it makes storage of the reference spectrum easier (because less memory is needed), and requires less resource for storing the reference spectrum. Also, limiting the number of reference peaks is beneficial because it allows the reference spectrum to be compared with the input spectrum quickly, which allows luggage to be scanned efficiently. The inventor has determined that using the above matching technique, the luggage scanning can still be performed accurately based on a relatively few numbers of peaks. Also, since the relatively smaller peaks in the reference spectrum may be noise, and they may not be present in the input spectrum (i.e., they may not match up with the input peaks), limiting the number of reference peaks allows matching of the input peaks to be performed accurately and efficiently, and reduces the effect of matching score penalization due to the smaller peaks. In some embodiments, the input spectrum may also be processed to reduce the number of input peaks (e.g., peaks that are relatively smaller in magnitude/intensity). This may allow noise in the input spectrum to be removed. Thus, as used in this specification, the term "input spectrum" may refer to an input spectrum in which the number of input peaks have not been reduced, or to a processed input spectrum in which the number of input peaks have been reduced. In some embodiments, the processor 204 may provide a user interface (e.g., graphics displayed in screen 206) that allows the user to input information for prescribing the number of reference peaks and/or the number of input peaks.

As illustrated in the above embodiments, the method 100 is simple to execute, and can be rapidly and accurately applied to unknown compounds to match them against a library of up to a few hundred, or more, reference compounds. Also, the embodiments of the technique described herein are more advantageous than spectrum matching algorithms (such as those in qualitative analysis in spectroscopy) that are for laboratory applications. Search methods, such as the Hanawalt search technique and the Fink search technique, are meant for laboratory applications where the quality of spectra is made very high (e.g., the input spectrum has high signal-to-noise ratio, and the number of reference peaks for comparison is high), and ample analysis time is available to compare experimental spectra to those of any one of thousands of compounds. However, they are not well suited for rapid comparison of materials to a library of a few hundred compounds. They are also not well suited for comparison of materials based on spectra with low signal-to-noise ratio, which may be the case with luggage scanning.

Although the above embodiments have been described with reference to detecting material(s) in luggage, in other embodiments, the technique described herein may be used to detect material(s) in other situations. For example, in other embodiments, the embodiments of the technique described herein may be used to detect material(s) in container (e.g., transport containers at seaport), in food (e.g., in food manufacturing process that involves mass production), or in biological subjects (e.g., humans, farm animals, etc.)

In other embodiments, instead of using the processor 204 for performing the entire method 100, the processor 204 may perform part(s) of the method 100. For example, in some embodiments, an additional processor (which may or may not be a part of a scanning machine) may be provided for performing step 102 of obtaining the input spectrum. In such cases, the additional processor is configured to transmit the input spectrum to the processor 204 for processing the input spectrum (step 104) and comparing the input spectrum with reference spectrum(s) (step 106). Also, in other embodiments, the additional processor 204 may perform steps 102, 104. In such cases, the additional processor is configured to process the input spectrum, and transmit the processed input spectrum to the processor 204, which compares the input spectrum with reference spectrum(s) (step 106). As used in this specification, the term "processor" may refer to one or more processing units, any of which may be implemented using software, hardware, or combination of both. For example, in some embodiments, a processing unit may be one or more microprocessors, one or more software applications, or any combination thereof. The processing unit(s) may perform the method 100 or part(s) of the method 100.

It should be noted that the method 100 is not limited to the embodiments described above, and that the method 100 can include other features and/or may have other variations. For example, in other embodiments, the method 100 can include matching of peak width, which could be represented by another term in the product of exponentials in the above equation. Also, in other embodiments, the equation described above may have other variations. For example, in other embodiments, the equation may be expressed in other manners, and/or may have other variables or expressions for representing any, or a combination, of the features described herein. Furthermore, in other embodiments, the processor 204 may provide a user interface (e.g., graphics displayed in screen 206) that allows a user to adjust a sensitivity of the comparison test for the presence a certain reference compound. For example, the sensitivity of the test for a certain compound may be set very high if desired. In some cases, this may be at the cost of specificity, but for certain applications in which secondary screening methods are available (such as baggage scanning for explosive materials or other hazardous materials), this would not be a significant limitation.

Figure 4A:
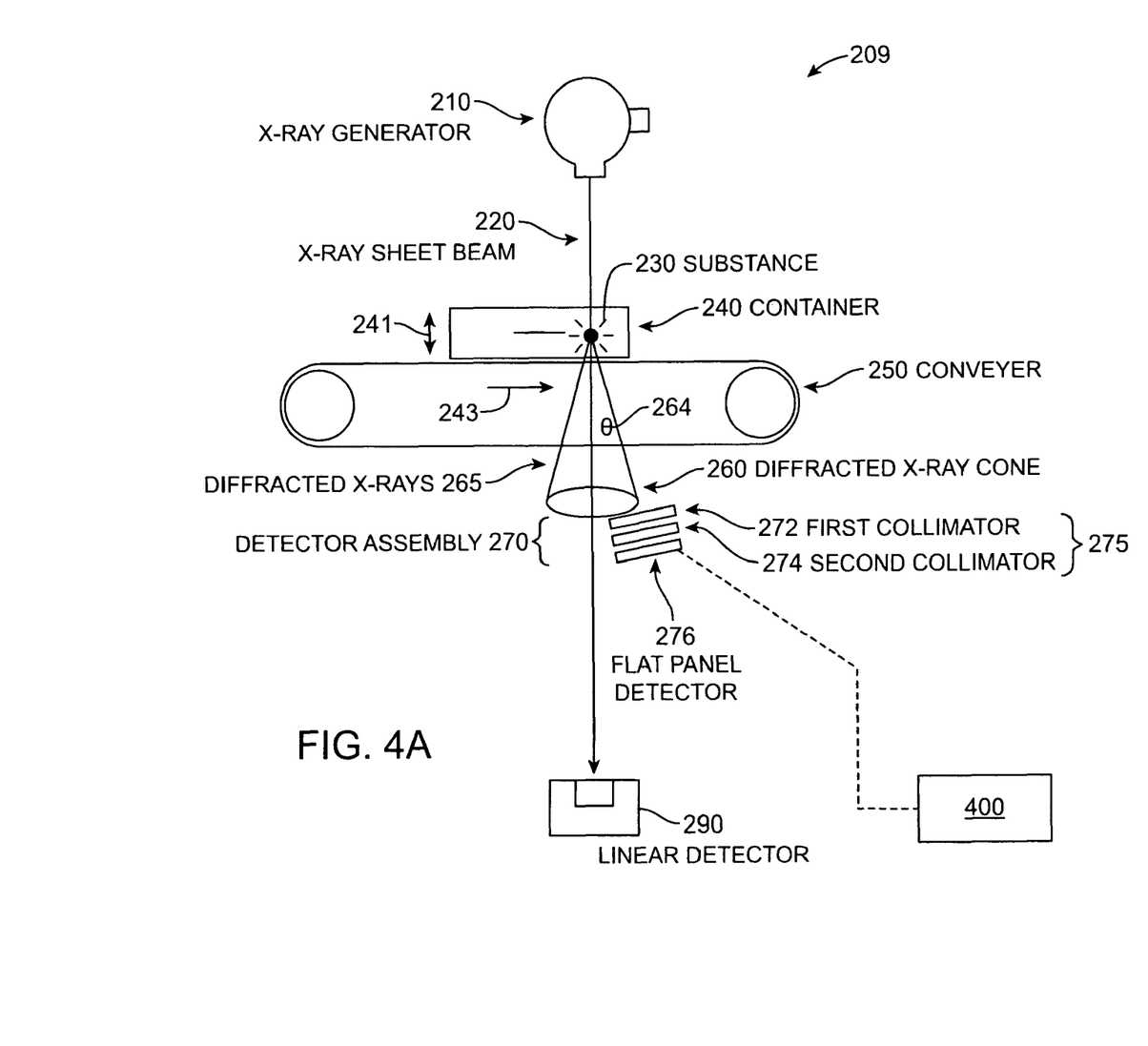
FIGS. 4A and 4B illustrate a luggage scanning system that incorporates embodiments described herein.
Figure 4B:
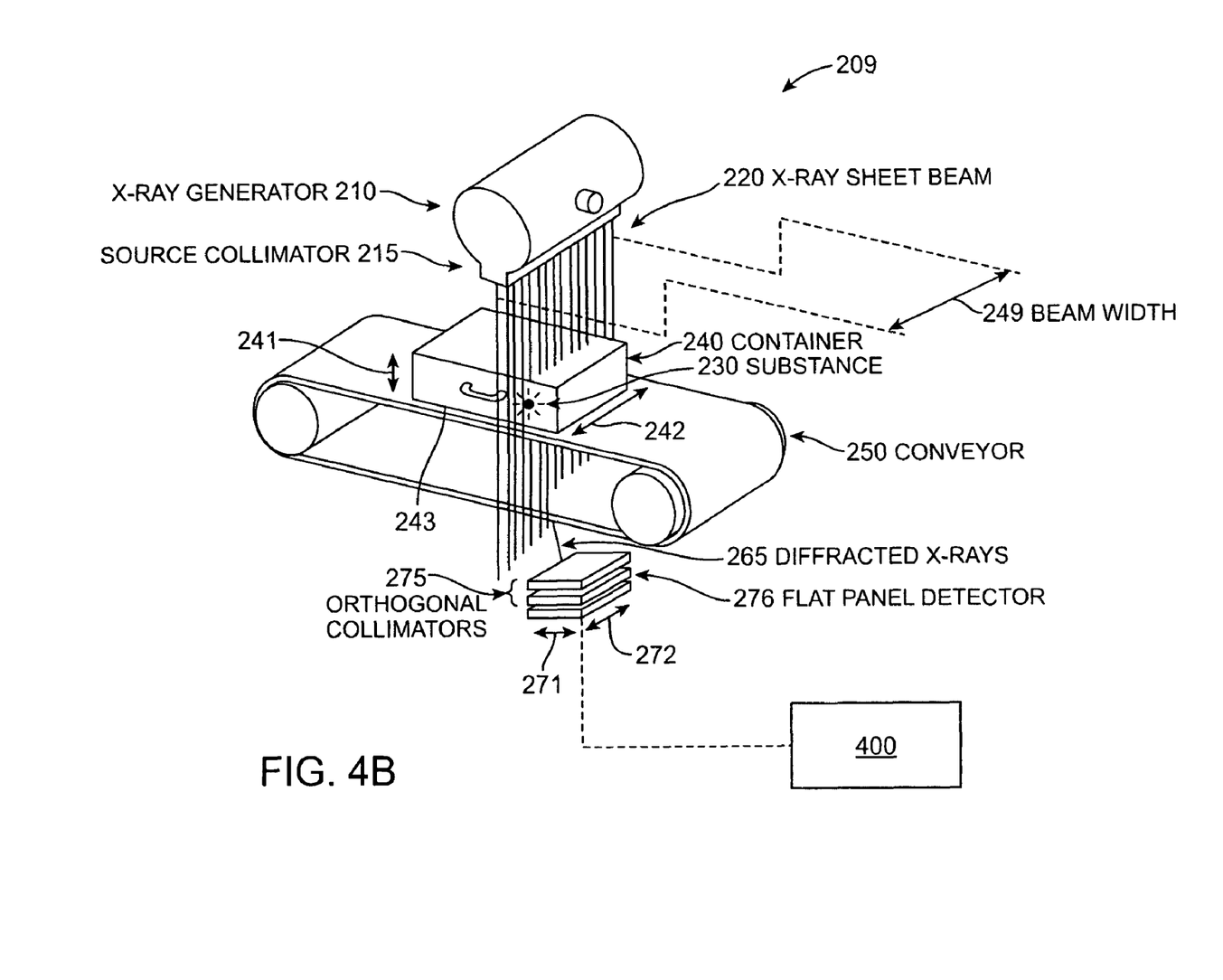

As discussed, the method 100 of FIG. 1 may be incorporated as a function of a scanning system. FIGS. 4A and 4B are a cross-section view and a perspective view, respectively, illustrating one embodiment of an x-ray diffraction system 209 that incorporates embodiments of the method 100 described herein. The x-ray diffraction system 209 includes an x-ray generator 210 having an x-ray source, a pair of collimators 275, and a two dimensional (2D) flat panel detector (FPD) array 276. The scanning system 209 also includes a processor 400 that is configured to perform various functions described herein. In some embodiments, the processor 400 may be the processor 204 described herein. In some embodiments, the processor 400 is configured to receive information regarding an input spectrum from the detector 276, and perform the method 100 described herein. The x-ray generator 210 is composed of an x-ray tube with a longitudinally extended target and one or more x-ray beams to generate an x-ray sheet beam 220, as further illustrated in FIG. 5. In one embodiment, the x-ray sheet beam 220 is composed of a continuous highly collimated x-ray sheet. In an alternative embodiment, the x-ray sheet beam 220 is composed of multiple close parallel-collimated sub-beams generated by source collimator 215.

Figure 5:
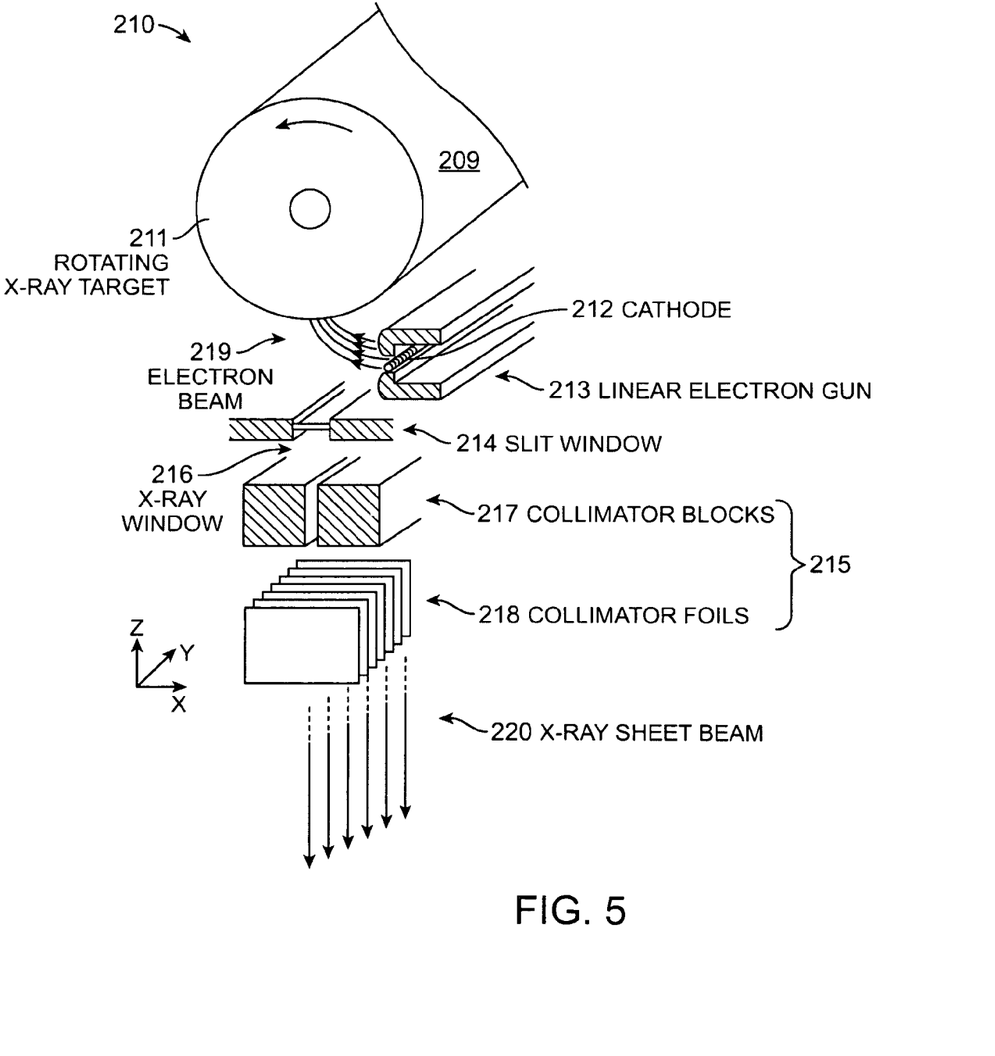
FIG. 5 illustrates some components of a luggage scanning system.

As illustrated by FIG. 5, source collimator 215 may include collimator blocks 217 that operate to limit beam divergence in the x-direction and collimator foils 218 that operate to limit beam divergence in the y-direction. A linear electron gun 213 may be used to generate an electron beam 219 using cathode 212. The electron beam 219 strikes the surface 209 of an elongated (e.g., in the range of 1 mm to 2 meters) rotating x-ray target (anode) 211 to generate x-rays that emanate through window 216. In one embodiment, target 211 has a width of approximately 1 meter. Collimator 215 may be used to collimate the x-rays to produce x-ray sheet beam 220. The shape of the beam may be configured by altering the shape of x-ray target 211. In one embodiment, for example, cuts may be made in surface 209 to produce a "picket-fence-like" x-ray sheet beam 220 composed of multiple, individual beams. It should be noted that alternative configurations for the x-ray generator 210 may be used to produce x-ray sheet beam 220. In one embodiment, the x-ray generator 210 has a large target 211 surface 209 area and can, therefore, operate at high peak and average power. If provided with adequate heat removal capacity, for example liquid cooling of the target 211 via a ferrofluidic seal, it can operate continuously with $\geq 100$ KW of input power. The rate at which a diffraction system can acquire data depends upon the detector efficiency. However, once the detector efficiency has been optimized the data acquisition rate scales directly with the available input x-ray power.

Referring again to FIGS. 4A and 4B, the x-ray sheet beam 220 is directed to a container 240 on a conveyor 250 as the conveyor moves the container 240 in direction 243 through the axis of the x-ray sheet beam 220. The x-ray sheet beam 220 passes vertically through the container 240 to be scanned as it moves along conveyor 250 in direction 243. Alternatively, the container 240 to be scanned need not be on a conveyor 250, but may be positioned under the x-ray sheet beam 220 through other means. In one embodiment, the width of the x-ray beam 220 is selected to cover, for example the whole width of container 240. Alternatively, the x-ray beam 220 may have a width greater than the width of conveyor 250. The x-ray sheet beam 220 may have widths, for example, in the approximate range of 2 mm to 2 meters as determined by the width of the x-ray target 211.

If the x-ray sheet beam 220 intercepts a crystalline material in the container 240 (e.g., a plastic explosive), x-ray photons are diffracted at an angle ($\theta$) 264 to the incident x-ray beam. The angle 264 depends upon the d-spacing of the atomic planes in the material. The trajectories of the diffracted photons lie on cones (e.g., cone 260) with half angle $\theta$ centered on the beam axis. The diffracted x-rays 265 are detected and their properties measured by a detector assembly 270 located below the conveyer 250 and displaced laterally from the path of the primary sheet beam so that the detector assembly 270 collects the diffracted x-rays 265. A linear detector 290 may be positioned underneath the conveyor at the primary axis of the x-ray sheet beam 220 to detect undiffracted components of the x-ray sheet beam 220. The linear detector (e.g., composed of a line of photoconducting diodes) measures the undiffracted x-ray beam and provides a reference signal and projection line scan image of container 240.

In one embodiment, the detector assembly 270 may include first and second collimators 272 and 274 and a flat panel detector 276. The flat panel detector 276 may have a conventional TFT structure with a scintillator or photoconductor x-ray direct conversion layer. In one embodiment, the conversion layer is amorphous and, in particular, may have a polycrystalline structure. Alternatively, the conversion layer may have other crystalline structures. The detector assembly 270 may be configured to have a narrow acceptance angle of approximately 0.2 degrees full width at half maximum (FWHM) by using one or more collimators placed in front of the flat panel detector 276. The collimation planes of the first collimators 272 plates (e.g., plate 283) and the second collimator 274 plates (e.g., plate 293) may be substantially orthogonal to each other. The collimators ensure that each pixel 279 of the flat panel detector 276 views a separate area of the beam, thus dividing the diffracted x-rays 265 into volume elements. In particular, first collimator 272 divides the x-ray sheet beam into individual vertical (e.g., beam direction 241 mapping to flat panel detector length 271) segments and second collimator 274 provides the angular resolution for accepting diffracted x-rays of a particular angle. Photons having a particular diffraction angle are selected by the angle of the collimators 275 and flat panel detector 276 with respect to the primary x-ray sheet beam 220. By tilting the second collimator 274 and flat panel detector 276 together, it is possible to scan through the diffraction spectrum in terms of diffraction angle. The first collimator 272 need not reside within the detector assembly 270, such that only the second collimator 274 and the flat panel detector 276 are movable. In an alternative embodiment, the plates of the first and second collimators may be integrated together to form a single collimator having orthogonal plates. Alternatively, other collimator arrangements known in the art may be used, for examples, hexagonal collimators.

By collecting the diffracted x-rays from each volume element (voxel), it is possible to detect, identify and physically locate substances (e.g., explosives) within container 240 as it is moved through the x-ray sheet beam 220. The method is substance-specific and sensitive, with sub-voxel detection capability because the substance does not need to fill an entire voxel to be identified. The requirement is merely that sufficient material of the substance is intersected by the x-ray sheet beam 220 to give a diffracted photon signal that is above the detector noise level.

The diffracted x-rays may be characterized in different ways, for examples, by wavelength dispersive (WD) diffraction and energy dispersive (ED) diffraction. In wavelength dispersive diffraction, an incident x-ray beam may be composed of monochromatized x-rays containing a narrow range of wavelengths typically 1% or less, centered upon an x-ray emission line characteristic of the x-ray target material, for example, a K-alpha line, to increase the photon flux in the monochromatized beam. The incident beam may be monochromatized, for examples, by diffraction off a crystal, by absorption edge filtering, via a graded multilayer mirror, or by other means known in the art. The latter has the advantage of improved x-ray collection efficiency.

Components for the above x-ray system 109 have been described in U.S. patent application Ser. No. 11/893,961, filed on Aug. 17, 2007, the entire disclosure of which is expressly incorporated by reference herein.

The device that can use the method 100 is not limited to the examples described. In other embodiments, the method 100 may be practiced with other types of testing machine, such as a medical machine for testing a patient, a food scanning machine for testing food, a transport container scanning system for testing contents in transport containers, etc.

Also, although the embodiments of the method 100 have been described with reference to spectrum identification, in other embodiments, the method 100 may be used for other signal patterns. For example, in other embodiments, the method 100 can be used to match any signal which includes a series of peaks such that peak positions are measured on a fixed (not relative) scale. Examples of such signals are spectra (peaks positioned according to a fixed energy scale), spatial patterns of peaks from a fixed edge, or time-series patterns of peaks from a standard zero time reference.

Computer System Architecture

Figure 6:
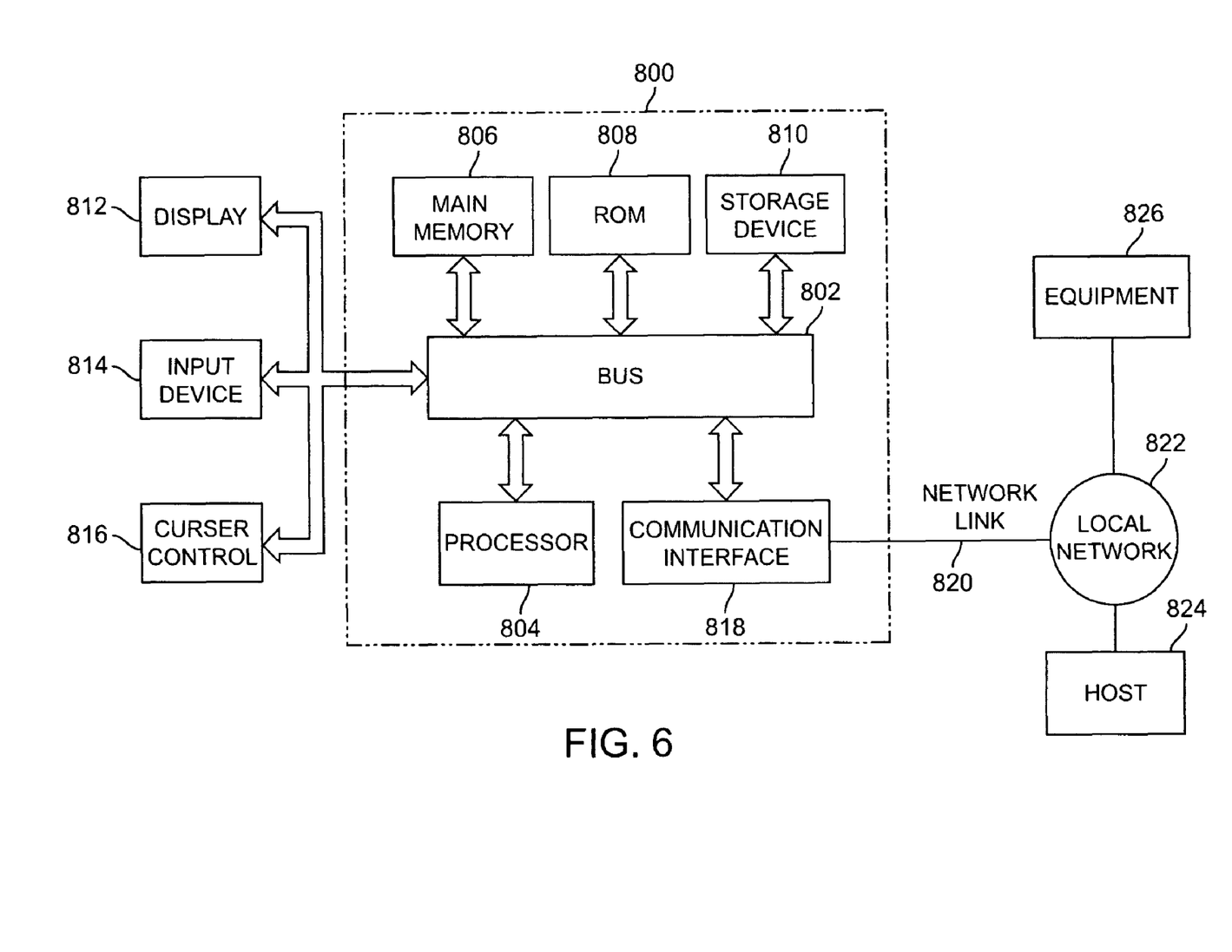
FIG. 6 is a block diagram of a computer system architecture, with which embodiments described herein may be implemented.

FIG. 6 is a block diagram that illustrates an embodiment of a computer system 800 upon which an embodiment of the invention may be implemented. Computer system 800 includes a bus 802 or other communication mechanism for communicating information, and a processor 804 coupled with the bus 802 for processing information. The processor 804 may be an example of the processor 204 of FIG. 2, or another processor that is used to perform various functions described herein. In some cases, the computer system 800 may be used to implement the processor 204. The computer system 800 also includes a main memory 806, such as a random access memory (RAM) or other dynamic storage device, coupled to the bus 802 for storing information and instructions to be executed by the processor 804. The main memory 806 also may be used for storing temporary variables or other intermediate information during execution of instructions to be executed by the processor 804. The computer system 800 further includes a read only memory (ROM) 808 or other static storage device coupled to the bus 802 for storing static information and instructions for the processor 804. A data storage device 810, such as a magnetic disk or optical disk, is provided and coupled to the bus 802 for storing information and instructions.

The computer system 800 may be coupled via the bus 802 to a display 812, such as a cathode ray tube (CRT) or a flat panel, for displaying information to a user. An input device 814, including alphanumeric and other keys, is coupled to the bus 802 for communicating information and command selections to processor 804. Another type of user input device is cursor control 816, such as a mouse, a trackball, or cursor direction keys for communicating direction information and command selections to processor 804 and for controlling cursor movement on display 812. This input device typically has two degrees of freedom in two axes, a first axis (e.g., x) and a second axis (e.g., y), that allows the device to specify positions in a plane.

The computer system 800 may be used for performing various functions (e.g., calculation) in accordance with the embodiments described herein. According to one embodiment, such use is provided by computer system 800 in response to processor 804 executing one or more sequences of one or more instructions contained in the main memory 806. Such instructions may be read into the main memory 806 from another computer-readable medium, such as storage device 810. Execution of the sequences of instructions contained in the main memory 806 causes the processor 804 to perform the process steps described herein. One or more processors in a multi-processing arrangement may also be employed to execute the sequences of instructions contained in the main memory 806. In alternative embodiments, hard-wired circuitry may be used in place of or in combination with software instructions to implement the invention. Thus, embodiments of the invention are not limited to any specific combination of hardware circuitry and software.

The term "computer-readable medium" as used herein refers to any medium that participates in providing instructions to the processor 804 for execution. Such a medium may take many forms, including but not limited to, non-volatile media, volatile media, and transmission media. Non-volatile media includes, for example, optical or magnetic disks, such as the storage device 810. Volatile media includes dynamic memory, such as the main memory 806. Transmission media includes coaxial cables, copper wire and fiber optics, including the wires that comprise the bus 802. Transmission media can also take the form of acoustic or light waves, such as those generated during radio wave and infrared data communications.

Common forms of computer-readable media include, for example, a floppy disk, a flexible disk, hard disk, magnetic tape, or any other magnetic medium, a CD-ROM, any other optical medium, punch cards, paper tape, any other physical medium with patterns of holes, a RAM, a PROM, and EPROM, a FLASH-EPROM, any other memory chip or cartridge, a carrier wave as described hereinafter, or any other medium from which a computer can read.

Various forms of computer-readable media may be involved in carrying one or more sequences of one or more instructions to the processor 804 for execution. For example, the instructions may initially be carried on a magnetic disk of a remote computer. The remote computer can load the instructions into its dynamic memory and send the instructions over a telephone line using a modem. A modem local to the computer system 800 can receive the data on the telephone line and use an infrared transmitter to convert the data to an infrared signal. An infrared detector coupled to the bus 802 can receive the data carried in the infrared signal and place the data on the bus 802. The bus 802 carries the data to the main memory 806, from which the processor 804 retrieves and executes the instructions. The instructions received by the main memory 806 may optionally be stored on the storage device 810 either before or after execution by the processor 804.

The computer system 800 also includes a communication interface 818 coupled to the bus 802. The communication interface 818 provides a two-way data communication coupling to a network link 820 that is connected to a local network 822. For example, the communication interface 818 may be an integrated services digital network (ISDN) card or a modem to provide a data communication connection to a corresponding type of telephone line. As another example, the communication interface 818 may be a local area network (LAN) card to provide a data communication connection to a compatible LAN. Wireless links may also be implemented. In any such implementation, the communication interface 818 sends and receives electrical, electromagnetic or optical signals that carry data streams representing various types of information.

The network link 820 typically provides data communication through one or more networks to other devices. For example, the network link 820 may provide a connection through local network 822 to a host computer 824 or to equipment 826 such as a radiation beam source or a switch operatively coupled to a radiation beam source. The data streams transported over the network link 820 can comprise electrical, electromagnetic or optical signals. The signals through the various networks and the signals on the network link 820 and through the communication interface 818, which carry data to and from the computer system 800, are exemplary forms of carrier waves transporting the information. The computer system 800 can send messages and receive data, including program code, through the network(s), the network link 820, and the communication interface 818.

Although particular embodiments have been shown and described, it will be understood that they are not intended to limit the present inventions, and it will be obvious to those skilled in the art that various changes and modifications may be made without departing from the spirit and scope of the present inventions. The specification and drawings are, accordingly, to be regarded in an illustrative rather than restrictive sense. The present inventions are intended to cover alternatives, modifications, and equivalents, which may be included within the spirit and scope of the present inventions as defined by the claims.

What is claimed:

1. A method for use in an object scanning process, comprising:
obtaining a reference spectrum that includes a plurality of reference peaks; and comparing the reference spectrum with an input spectrum that has a plurality of input peaks;
wherein a number of the reference peaks is less than eight.

2. The method of claim 1, wherein the act of comparing is performed to determine a degree of similarity between the input spectrum and the reference spectrum.

3. The method of claim 1, wherein the act of comparing is performed using a reverse-matching technique in which one of the reference peaks from the reference spectrum is compared with multiple ones of the plurality of input peaks from the input spectrum.

4. The method of claim 1, wherein the act of comparing comprises determining a score that represents a degree of similarity between the input spectrum and the reference spectrum.

5. The method of claim 4, wherein the score is based at least on a difference between a position of one of the reference peaks and a position of one of the input peaks, and a ratio calculated using a magnitude of the one of the reference peaks and a magnitude of the one of the input peaks.

6. The method of claim 4, wherein the score is determined by weighting a matched peak that has a higher magnitude more than a matched peak that has a lower magnitude.

7. The method of claim 4, wherein the act of comparing further comprises normalizing the score.

8. The method of claim 1, wherein the input spectrum is for an object that is being scanned by a luggage scanning machine.

9. The method of claim 1, wherein the act of comparing is performed using a function:

$$\text{score} = \sum_i \left[ y_{r,i} \cdot \sum_j \left( e^{-\left(\frac{x_{r,i} - x_{m,j}}{a}\right)^2} e^{-\left(\frac{\ln(y_{r,i}/y_{m,j})}{b}\right)^2} \right) \right],$$

or a variation thereof, wherein $(x_{r,i}, y_{r,i})$ is a position and magnitude of an i'th peak in the reference spectrum, $(x_{m,j}, y_{m,j})$ is a position and magnitude of a j'th peak in the input spectrum, and values a and b are user selected inputs.

10. A system for use in an object scanning process, comprising:
a processor, wherein the processor is configured for:
obtaining a reference spectrum that includes a plurality of reference peaks; and
comparing the reference spectrum with an input spectrum that has a plurality of input peaks;
wherein a number of the reference peaks is less than eight.

11. The system of claim 10, wherein the processor is configured for performing the act of comparing to determine a degree of similarity between the input spectrum and the reference spectrum.

12. The system of claim 10, wherein the processor is configured for performing the act of comparing by using a reverse-matching technique.

13. The system of claim 10, wherein the processor is configured for performing the act of comparing by determining a score that represents a degree of similarity between the input spectrum and the reference spectrum.

14. The system of claim 13, wherein the score is based at least on a difference between a position of one of the reference peaks and a position of one of the input peaks, and a ratio calculated using a magnitude of the one of the reference peaks and a magnitude of the one of the input peaks.

15. The system of claim 14, wherein the processor is configured to determine the score by weighting a matched peak that has a higher magnitude more than a matched peak that has a lower magnitude.

16. The system of claim 13, wherein the processor is further configured for normalizing the score.

17. The system of claim 10, wherein the input spectrum is for an object that is being scanned by a luggage scanning machine.

18. The system of claim 10, wherein the processor is configured to perform the act of comparing by using a function:

$$\text{score} = \sum_i \left[ y_{r,i} \cdot \sum_j \left( e^{-\left(\frac{x_{r,i} - x_{m,j}}{a}\right)^2} e^{-\left(\frac{\ln(y_{r,i}/y_{m,j})}{b}\right)^2} \right) \right],$$

or a variation thereof, wherein $(x_{r,i}, y_{r,i})$ position and magnitude of an i'th peak in the reference spectrum, $(x_{m,i}, y_{m,i})$ is a position and magnitude of a j'th peak in the input spectrum, and values a and b are user selected inputs.

19. A method for use in an object scanning process, comprising:
obtaining a reference spectrum that includes a plurality of reference peaks;
comparing one of the reference peaks with a plurality of input peaks from an input spectrum;
comparing another one of the reference peaks with the plurality of input peaks from the input spectrum; and
determining a degree of similarity between the reference spectrum and the input spectrum using a result from the acts of comparing.

20. The method of claim 19, wherein a number of the reference peaks is less than eight.

21. The method of claim 19, wherein the acts of comparing are performed using a reverse-matching technique.

22. The method of claim 19, wherein the act of determining the degree of similarity comprises determining a score.

23. The method of claim 22, wherein the score is determined based at least on a difference between a position of the one of the reference peaks and a position of one of the input peaks, and a ratio calculated using a magnitude of the one of the reference peaks and a magnitude of the one of the input peaks.

24. The method of claim 22, wherein the score is determined by weighting a matched peak that has a higher magnitude more than a matched peak that has a lower magnitude.

25. The method of claim 22, wherein the act of determining the degree of similarity further comprises normalizing the score.

26. The method of claim 19, wherein the input spectrum is for an object that is being scanned by a luggage scanning machine.

27. The method of claim 19, wherein the acts of comparing and the act of determining the degree of similarity are performed using a function:

$$\text{score} = \sum_i \left[ y_{r,i} \cdot \sum_j \left( e^{-\left(\frac{x_{r,i} - x_{m,j}}{a}\right)^2} e^{-\left(\frac{\ln(y_{r,i}/y_{m,j})}{b}\right)^2} \right) \right],$$

or a variation thereof, wherein $(x_{r,i}, y_{r,i})$ is a position and magnitude of an i'th peak in the reference spectrum, $(x_{m,j}, y_{m,j})$ is a position and magnitude of a j'th peak in the input spectrum, and values a and b are user selected inputs.

28. A system for use in an object scanning process, comprising:
a processor, wherein the processor is configured for:
obtaining a reference spectrum that includes a plurality of reference peaks;
comparing one of the reference peaks with a plurality of input peaks from an input spectrum;
comparing another one of the reference peaks with the plurality of input peaks from the input spectrum; and
determining a degree of similarity between the reference spectrum and the input spectrum using a result from the acts of comparing.

29. The system of claim 28, wherein a number of the reference peaks is less than eight.

30. The system of claim 28, wherein the processor is configured to perform the acts of comparing using a reverse-matching technique.

31. The system of claim 28, wherein the processor is configured to determine a score that represents the degree of similarity.

32. The system of claim 31, wherein the processor is configured to determine the score based at least on a difference between a position of the one of the reference peaks and a position of one of the input peaks, and a ratio calculated using a magnitude of the one of the reference peaks and a magnitude of the one of the input peaks.

33. The system of claim 31, wherein the processor is configured to determine the score by weighting a matched peak that has a higher magnitude more than a matched peak that has a lower magnitude.

34. The system of claim 31, wherein the processor is configured for normalizing the score.

35. The system of claim 28, wherein the input spectrum is for an object that is being scanned by a luggage scanning machine.

36. The system of claim 28, wherein the processor is configured to perform the acts of comparing and the act of determining the degree of similarity using a function:

$$\text{score} = \sum_i \left[ y_{r,i} \cdot \sum_j \left( e^{-\left(\frac{x_{r,i}-x_{m,j}}{a}\right)^2} e^{-\left(\frac{\ln(y_{r,i}/y_{m,j})}{b}\right)^2} \right) \right],$$

or a variation thereof, wherein $(x_{r,i}, y_{r,i})$ is a position and magnitude of an i'th peak in the reference spectrum, $(x_{m,j}, y_{m,j})$ is a position and magnitude of a j'th peak in the input spectrum, and values a and b are user selected inputs.

37. A method for use in an object scanning process, comprising:
obtaining a reference spectrum that includes a reference peak;
comparing the reference peak with an input peak from an input spectrum, wherein the act of comparing comprises determining information regarding a positional match between the reference peak and the input peak, and information regarding a magnitude match between the reference peak and the input peak; and
using a result from the act of comparing to determine a degree of similarity between the reference spectrum and the input spectrum.

38. The method of claim 37, wherein the information regarding the positional match comprises a difference between a position of the reference peak and a position of the input peak.

39. The method of claim 37, wherein the information regarding the magnitude match comprises a difference between a magnitude of the reference peak and a magnitude of the input peak.

40. The method of claim 37, wherein the act of determining the degree of similarity comprises determining a score.

41. The method of claim 40, wherein the score is determined by weighting a matched peak that has a higher magnitude more than a matched peak that has a lower magnitude.

42. The method of claim 40, wherein the act of determining the degree of similarity further comprises normalizing the score.

43. A system for use in an object scanning process, comprising:
a processor, wherein the processor is configured for:
obtaining a reference spectrum that includes a reference peak;
comparing the reference peak with an input peak from an input spectrum, wherein the act of comparing comprises determining information regarding a positional match between the reference peak and the input peak, and information regarding a magnitude match between the reference peak and the input peak; and
using a result from the act of comparing to determine a degree of similarity between the reference spectrum and the input spectrum.

44. The system of claim 43, wherein the information regarding the positional match comprises a difference between a position of the reference peak and a position of the input peak.

45. The system of claim 43, wherein the information regarding the magnitude match comprises a difference between a magnitude of the reference peak and a magnitude of the input peak.

46. The system of claim 43, wherein the processor is configured for determining the degree of similarity by determining a score.

47. The system of claim 46, wherein the processor is configured to determine the score by weighting a matched peak that has a higher magnitude more than a matched peak that has a lower magnitude.

48. The system of claim 46, wherein the processor is further configured for normalizing the score.

* * * * *